(12) United States Patent
Torfs et al.

(10) Patent No.: US 6,788,413 B2
(45) Date of Patent: Sep. 7, 2004

(54) METHOD FOR CHARACTERIZING THE APPEARANCE OF A PARTICULAR OBJECT, FOR PREDICTING THE APPEARANCE OF AN OBJECT, AND FOR MANUFACTURING AN OBJECT HAVING A PREDETERMINED APPEARANCE WHICH HAS OPTIONALLY BEEN DETERMINED ON THE BASIS OF A REFERENCE OBJECT

(75) Inventors: Jan C. Torfs, Terneuzen (NL); Gerrit J. Brands, Terneuzen (NL); Eric G. Goethals, Bruges (BE); Evelien M. Dedeyne, Merelbeke (BE)

(73) Assignee: Dow Global Technologies Inc., Midland, MI (US)

( * ) Notice: Subject to any disclaimer, the term of this patent is extended or adjusted under 35 U.S.C. 154(b) by 190 days.

(21) Appl. No.: 09/990,687

(22) Filed: Nov. 9, 2001

(65) Prior Publication Data

US 2002/0118357 A1 Aug. 29, 2002

(30) Foreign Application Priority Data

Nov. 20, 2000 (EP) .......................................... 00125189

(51) Int. Cl.[7] ............................................. G01N 21/25
(52) U.S. Cl. ...................... 356/408; 356/402; 356/405
(58) Field of Search ................................. 356/402, 408, 356/421, 422, 425

(56) References Cited

U.S. PATENT DOCUMENTS

| 4,479,718 | A | | 10/1984 | Alman ....................... 356/405 |
| 4,711,580 | A | | 12/1987 | Venable ...................... 356/406 |
| 5,231,472 | A | | 7/1993 | Marcus et al. .............. 356/402 |
| 5,592,294 | A | | 1/1997 | Ota et al. ................... 356/402 |
| 5,668,633 | A | * | 9/1997 | Cheetam et al. ............ 356/402 |
| 5,929,998 | A | * | 7/1999 | Kettler et al. ............... 356/405 |
| 6,166,814 | A | * | 12/2000 | Pringle ....................... 356/445 |
| 6,249,751 | B1 | * | 6/2001 | Asaba et al. .................. 702/76 |
| 6,362,885 | B1 | * | 3/2002 | Osumi et al. ............... 356/402 |

FOREIGN PATENT DOCUMENTS

| DE | 42 43 885 | 6/1994 | ............. G01J/3/46 |
| EP | 0 375 317 | 6/1990 | ............. G01J/3/50 |
| EP | 0 964 244 | 12/1999 | .......... G01N/21/47 |
| GB | 1103950 | 2/1968 | ............. G01J/3/46 |

* cited by examiner

Primary Examiner—Frank G. Font
Assistant Examiner—Layla Lauchman

(57) ABSTRACT

The surface contribution to appearance of an object is characterized using a plurality of viewing and illumination angles. The color determining and surface contribution are determined to aid in the predicting of the appearance of an object as well as matching an object to another object.

23 Claims, 2 Drawing Sheets

Figure 1:
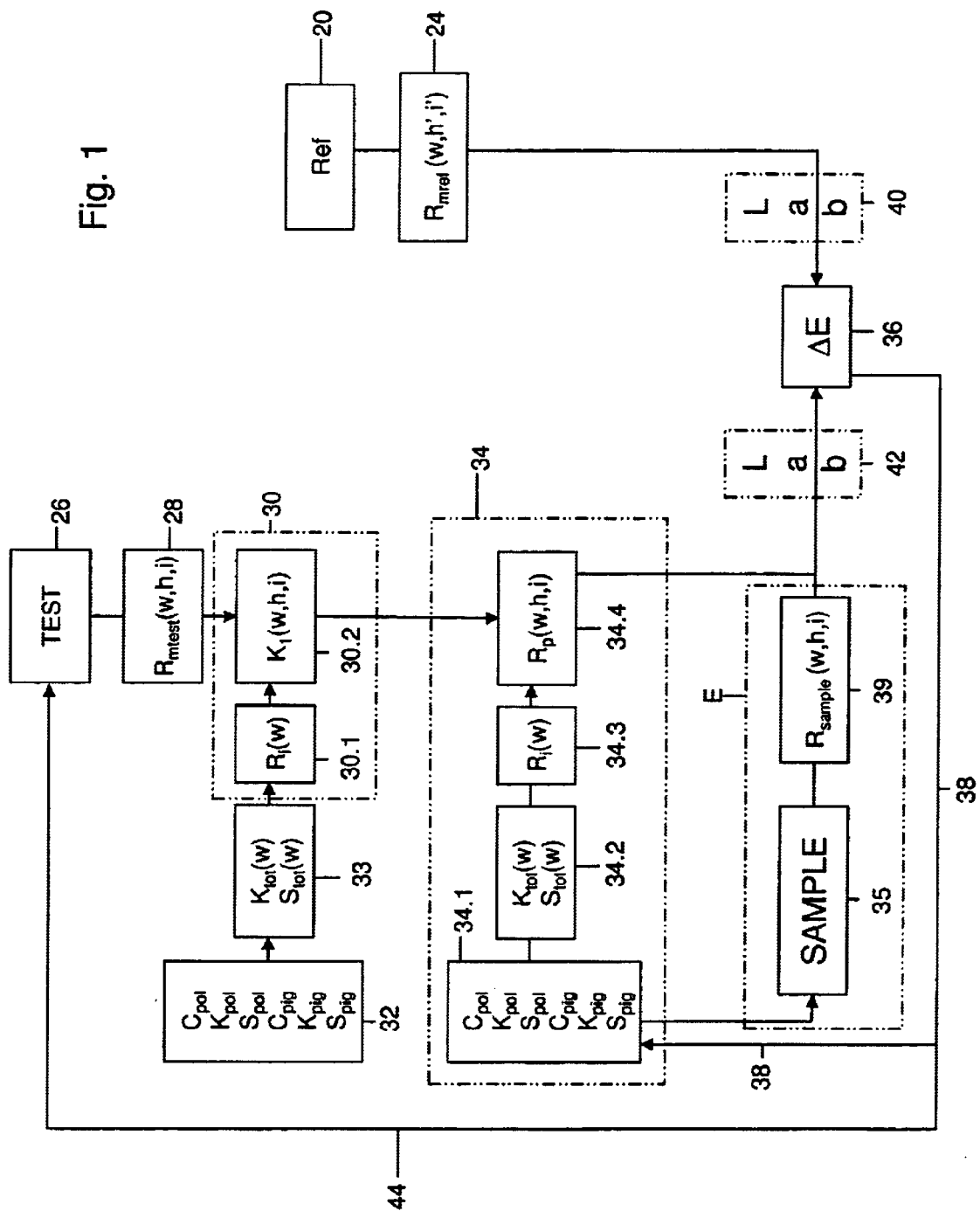

METHOD FOR CHARACTERIZING THE APPEARANCE OF A PARTICULAR OBJECT, FOR PREDICTING THE APPEARANCE OF AN OBJECT, AND FOR MANUFACTURING AN OBJECT HAVING A PREDETERMINED APPEARANCE WHICH HAS OPTIONALLY BEEN DETERMINED ON THE BASIS OF A REFERENCE OBJECT

CROSS-REFERENCE TO PRIOR APPLICATION

This application claims the benefit of European Patent Application No. 00125189.1 filed Nov. 20, 2000.

BACKGROUND OF THE INVENTION

The invention relates to a method for characterizing, by means of a measurement, the appearance of an object, more particularly, to a method for characterizing the contribution of the surface to the appearance of an object and for predicting the object's surface appearance.

Currently, many products are manufactured from plastic. These products have a particular appearance that depends on how the combination of the object's color and surface texture is perceived by the human eye. The appearance will in general be different when the sample is rotated relative to illumination and/or observer. This is caused by a number of factors, both internal factors such as the kind of material from which the object is manufactured, manufacturing conditions, the colorants (concentrations and types) used in the material, and surface factors, for example, the surface texture, of the object.

Surface texture is one factor considered when an object is to be manufactured. It may, for instance, be required that the surface's texture has a leather-like character, such as used in interiors of cars. This surface texture also affects the appearance.

There is are known methods for predicting what the color of an object will be (see: Practical Color Measurement, Anni-Berger-Schunn, Joseph W. Goodman, ed. J. Wiley, New York, 1994) based on the kind of material (often plastics such as polymers) and the colorants used for manufacturing the object.

A leading theory, with corresponding equations, which is used to match color is referred to as Kubelka-Munk. Many improved theories have been derived based on this theory. The Kubelka-Munk theory is based on diffuse illumination, which can be understood as light coming from all or at least many angles simultaneously. The experimental technique to create such an illumination uses a so-called integrating sphere and the data measured on such spectrophotometric equipment is treated using the Kubelka-Munk theory. In a spectrophotometer, the detector is usually placed in this integrating sphere at an angle of zero or 8 degrees relative to the perpendicular of the sample to be measured. For the user of such equipment, there is little practical possibility to change angles of viewing or illumination in this equipment. Therefore, the reflectance values measured in this classical way are considered angle-independent. This is essentially true, although in principle, a redesign of these spectrophotometers with a different viewing angle may lead to a slightly different reflectance value.

The kind of plastic in its natural state and color, as well as the colorants mentioned, serve as a basis in Kubelka-Munk theory for the prediction of an object's final appearance. However, this prediction is often poorly related to visual perception. For example, the effect of surface characteristics such as gloss on appearance is often not or poorly predicted, and also the effect of changes in illumination and/or viewing angle relative to the surface is not predicted. The integrating sphere used in the Kubelka-Munk (K-M) theory in general also masks the surface effects, for example, the effects of gloss and texture, to a large extent. Thus, neither the K-M theory, as used today, nor its associated measurement is able to predict surface characteristics such as gloss and texture. As a consequence, use of the known art of color prediction in general predicts a color, which is presumed to give a preselected appearance, but in reality more probably results in an appearance totally different than that seen by the human eye. This is particularly true when attempting to match the appearance of different materials.

For example, when a color standard made in polypropylene is used to match a sample to be formulated in a different material, for example ABS (Acrylonitrile Butadiene Styrene copolymer) a predicted formulation using existing color formulation techniques will almost always lead to a visibly unacceptable match. It happens frequently that the measurement of the standard and formulated sample with such equipment indicates that a color difference is small or negligible whereas visible differences are clearly much larger and often unacceptable. Another related problem is that while a visible match can be obtained under one viewing angle, rotation of the sample and reference material may lead to visible appearance differences at some other angles.

More particularly, this means, for instance in the car industry, that it is not easy to manufacture two or more plastic objects having the same appearance such as matching the appearance of one part of the instrument panel with the appearance of another part of the instrument panel made of another material. Thus, an observer notices differences in appearance. In another example, it is not possible to give, for instance, the automotive instrument panel the same appearance as the leather upholstery of a seat. In this case, too, a user of the car notices appearance differences. As mentioned, there are techniques known per se for measuring the color of an object. This technology can also be used to predict what the effects will be of the choice of a particular plastic and colorants (and other additives) on the color of an object to be manufactured. In this way, with existing techniques, an object such as the automotive instrument panel can be manufactured which, as regards its color, corresponds as much as possible with the color of the reference object, such as the leather-upholstered seat mentioned. It has been found, however, that the user still notices differences in appearance.

SUMMARY OF THE INVENTION

An object of the invention is to provide a solution to the problems outlined above. In the present invention, directional or collimated light (that is, more or less narrow beam of light which has distinct (although possible somewhat spread) viewing and illumination angle(s)) is used. Viewing angle can be chosen by the user and is a variable that may have significant effect on the result. Measured reflectance data are strongly dependent on these angles (that is, are "angle dependent"), and are related to the observed appearance. In contrast, the known systems are angle independent systems or, fixed angle systems, that do not allow to the characterization, measurement or prediction of appearance as observed under a variety of conditions, met in practice.

Accordingly, in a first aspect, the present invention is a method for characterizing the contribution of the surface to the appearance of an object. This method is characterized in that the surface contribution to appearance, or the surface reflection $k_1(w,h,i)$, is calculated from a plurality of reflectance values $R_m(w,h,i)$ which are established for at a light frequency w and a plurality of combinations of viewing angle(s) (h), and illumination angle(s) (i). The calculation of $k_1(w,h,i)$ from $R_m(w,h,i)$ involves the use of the color determining parameters of the material. Preferably, $k_1(w,h,i)$ is calculated at a number of wavelengths, w, covering the visible spectrum, and a plurality (at least two) combinations of viewing and illumination angles in order to have a more or less complete description of the surface contribution to the appearance. Once the surface contribution to the appearance has been determined, the appearance of the sample to the reference material can be subsequently matched by, for example, changing the colorants or other additives.

The invention is based inter alia on the insight that the appearance of the object depends not only on colorant loading and base material, but also on the angle at which the object is viewed by the human eye and the condition of illumination of the object. The effect that the viewing and illumination angles have on the surface and hence the appearance as perceived by the viewer is taken into account. The illumination is preferably directional light although illumination by a combination of directional and diffuse light may be employed.

In this invention, use is made of the formulae in which the surface reflection $k_1(w)$ was assumed to be independent of the viewing and illumination angles (h),(i). The formulae are generally based on diffuse illumination that is obtained with an integrating sphere. (See: Practical color Measurement by A Berger-Schunn page 114. Or: Judd, Wyszecki, Color in business, science and Industry, J. Wiley, New York, 1975, p 420–461). In the present invention, however, the formulae known per se (or future formulae still to be developed) are used for determining, for each predetermined viewing angle (h) and predetermined illumination angle (i), what the surface reflection $k_1(w,h,i)$ is for these angles. It has been found that in this way these formulae can be used for characterizing the appearance of an object and used for predicting what the appearance of an object will be as well as matching an object's appearance to a preselected appearance, either an actual reference object whose appearance is desired or a virtual object having a desired appearance. There is more than one color theory. The invention is not limited to an equation of a specific color theory.

In this method, a plurality of (that is, at least two) reflectance values $R(w,h,i)$ for a plurality of sets of (h,i) of viewing and illumination angles wherein each set comprises a viewing angle (h) and an associated illumination angle (i) are measured and a plurality of reflection values $k_1(w,h,i)$ corresponding with the respective measured reflectance values $R(w,h,i)$ are calculated. The surface reflections $k_1(w,h,i)$ associated with the viewing and illumination angles are calculated from each value of measured reflectance value $R_m(w,h,i)$ associated with these viewing and illumination angles and the value of $R_1(w)$.

In another aspect of the present invention, an object's appearance is predicted from both color determining ("internal") parameters of the material (which are dependent on the kind of material and the optional colorants from which the object is manufactured) and also the value of the surface reflection $k_1(w,h,i)$ for predetermined viewing and illumination angles. Preferably, this method is further characterized in that based on the color determining parameters of the material from which the object is manufactured and on the basis of a plurality of reflection values $k_1(w,h,i)$, it is predicted what the appearance of the object will be such as it is observed for the plurality of sets (h,i) of predetermined viewing and illumination angles.

Combining the method according to the invention for characterizing the appearance of an object on the one hand and predicting the appearance of an object on the other hand provides a sound basis for appearance matching.

In such method, the reflectance value of a reference object $R_{mref}(w,h,i)$ or a number of desired reflectance values at a range of wave lengths associated and/or viewing/illumination angles is determined. This may be established from actual measurements of an object (that is, a real reference object) or a theoretical appearance that is desired (a "virtual" object). Then, a sample object is produced that is selected to have reflectance value or values that approximate the predetermined value or values. This method comprises the steps of:

A. measuring or otherwise setting the reflectance values of a reference object whose appearance is to be matched at a plurality of predetermined viewing (h) and illumination (i) angles;

B. measuring the reflectance value $R_{mtest}(w,h,i)$ of a test object manufactured from a pre-selected material having a pre-selected amount and type of colorant(s) and/or other additive(s) using a pre-selected method of manufacture;

C. calculating the surface contribution to appearance or the reflection value(s) $k_1(w,h,i)$ of the test object from reflectance value(s) $R_{mtest}(w,h,i)$ associated with the predetermined viewing (h) and under illumination (i) angles;

D. making a sample object predicted to have the reflectance value(s) $R_p(w,h,i)$ which are predicted using the $k_1(w,h,i)$ values measured in C. with the desired reflectance value (s) $R_{mref}(w,h,i)$ of the reference object;

E. comparing the reflectance values measured on the sample object from step D. with that of the reflectance value of the reference object;

F. repeating, as desired, steps B., C., D., or E. using different selection of the amount or type of colorants, other additives or manufacturing process until the surface appearance of the first and second object are acceptable. This choice is made based on the calculated $k_1(w,h,i)$ and selected combination of internal factors such as the type and amount of colorants which should approximate the measured reflectance value of the reference object.

In a preferred embodiment, the test object produced in step B. is produced having a black color for determining the surface reflection $k_1(w,h,i)$. In that case, the surface reflection has, with respect to the color of the object, a relatively greater influence on the appearance, and can therefore be accurately determined in an easy manner. Using the $k_1(w,h,i)$ value measured from the black object, it is then possible to more easily select the internal factors such as colorants to match appearances, both surface appearance and color. In a preferred embodiment, steps B. and C. may be repeated to result in a different surface reflection k1 that leads to a better match of the reflectance values prior to preceding to step D. et seq.

Using the method of the present invention, it is possible to measure and predict the internal (for example, choice of the material, including the type and amount of colorants and/or other additives) and surface factors that contribute to appearance and modify either or both factors to result in the desired appearance. The appearance of the test and reference objects can be matched by changing either or both the surface characteristics or internal factors. It is this combination of surface and internal factors that give an object its appearance and this combination is selected to result in the same appearance even if each factor between the test and references objects are not equivalent.

Color theory, which equations have been developed for diffuse light (that is, assumed to be independent of the viewing and the illumination angles) are, for the purposes of this invention, used with directional light and a plurality of viewing and/or illumination angle(s). Thus, according to the present invention, the appearance (that is, the total of the surface and internal contributions) of a number of objects can be matched essentially over the entire range of viewing angles and wavelengths at which the objects may be viewed. In the prior art methods, it was not practical to match more than color of the objects as measured by diffuse spectrometry and then, the appearance varied between objects as the viewing angles and wavelengths changed.

There are essentially limitless combinations of material, colorants, additives and manufacturing processes that affect appearance. For example, the surface contribution to appearance or the surface reflection $k_1(w,h,i)$ may be set based on the choice of material and a surface texture for the object. Alternatively, the surface texture and the kind of material may be fixed and, in this case, the selection of the colorants or other additives is modified to achieve an appearance match.

It is also possible, particularly where the appearance match is not sufficiently close, that the surface texture and/or the type of material will need to be adjusted. In such case, the value of $k_1(w,h,i)$ is determined again according to step A and steps B, C, D, E and F may have need to be repeated more than a few times; particularly, where the appearances or the objects being matched are to match at a multitude combinations of viewing and illumination angles.

According to a preferred embodiment of the present invention, the predetermined reflectance value(s) $R_{mref}(w,h,i)$ is determined on the basis of a reference object. In most cases, this reference object is an existing part; for example, leather seat, that is required to be matched; for example, by the automotive instrument panel. However, the reference object may also be virtual with its reflectance values merely theoretical, that is, set by the desired appearance. By the method of the present invention, an appearance match is obtained between the reference object or existing part and the object to be manufactured.

The present invention has a number of obvious applications, such as matching adjoining parts made from different materials. Thus, two different polymers such as ABS and polypropylene can be made to have the same appearance over the entire range at which such objects are to be viewed. It should also be possible to characterize the surface appearance and to predict and match the appearance of transparent and translucent objects.

DETAILED DESCRIPTION OF THE INVENTION

The many aspects of the present invention will be further elucidated with reference to the drawings.

Figure 2:
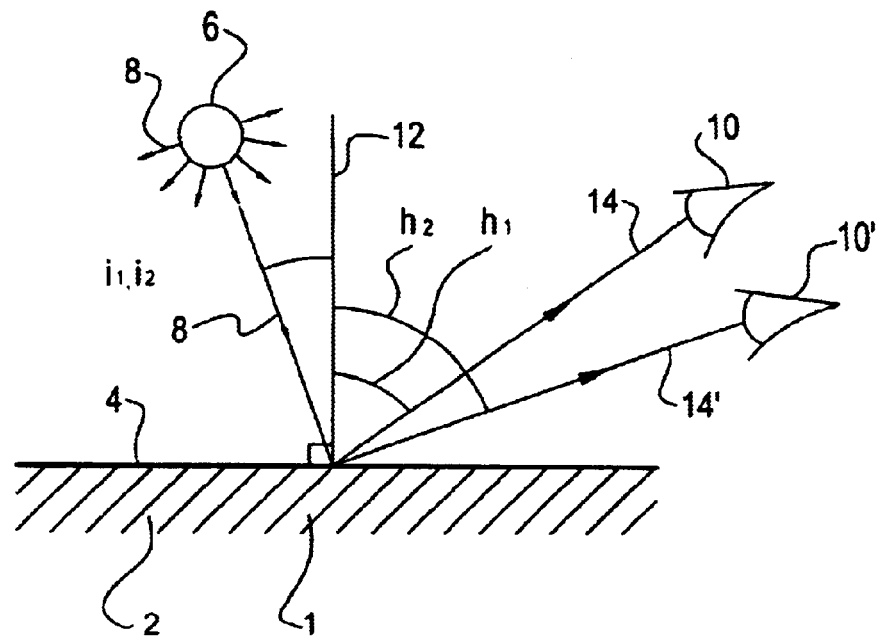
Figure 3:
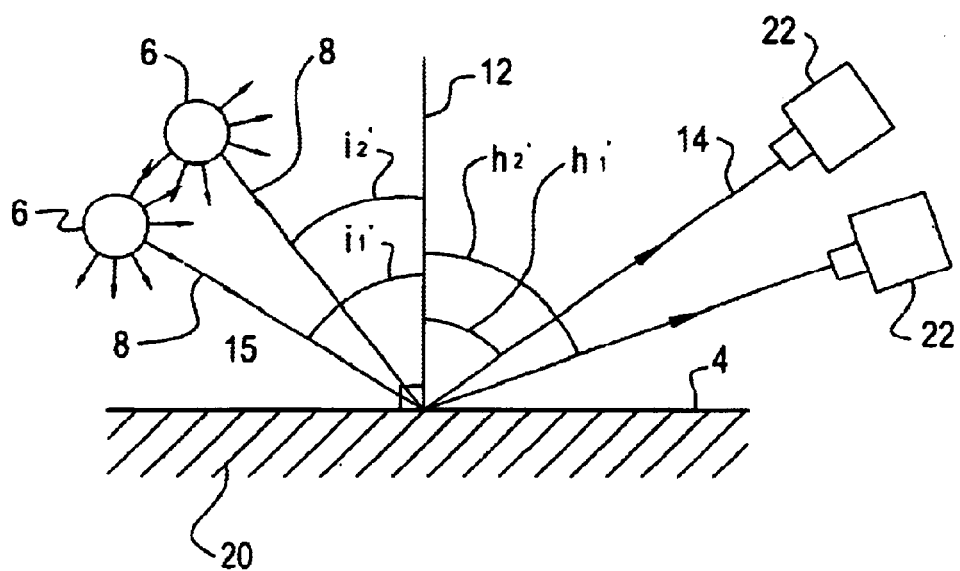

In the drawings:

FIG. 1 shows a flow diagram in which various methods according to the invention are represented;

FIG. 2 schematically shows two observations of the appearance of an object;

FIG. 3 shows a measuring arrangement for measuring a number of reflectance values or a curve of reflectance values of an object.

It should be noted that, in FIGS. 2 and 3, the plane formed by the illumination and the perpendicular to the surface, does not have to be the same as the plane formed by the viewing position and the perpendicular to the surface, even though the schematic drawings show all these positions to be in one plane.

The present invention is concerned with the appearance of an object taking into account the surface texture and/or gloss of the object (that is, surface properties). The appearance of an object is dependent on the viewing angle (h) and the illumination angle (i) as well as other phenomena. A viewing angle (h) observed at a specific illumination having an illumination angle (i) will be noted as (h,i). A viewing angle observed at multiple illumination angles is also noted as (h,i). In FIG. 2, an object 1 is shown which is a polymer 2. Object 1 can be essentially any material such as, metal, painted wood or metal or other material in addition to the polymer 2 illustrated. The object has a surface 4. In the example, the object is illuminated with a light source 6 under the illumination angle ($i_1$). This light will reflect and/or scatter on the surface 4 and may be partially re-emitted by the material 2. The resulting total reflected light in the direction $h_1$ can be observed by an observer 10 located at this viewing angle ($h_1$). In this example, the viewing angle ($h_1$) is the angle enclosed between a normal 12 to the surface 4 of the object and the line of view 14 of the observer 10.

The observer 10 will observe the object 1 as having a particular appearance. This appearance can be described as a combination of color (light re-emitted from the inside of the material) and surface reflection and scattering. The appearance is determined by a number of factors. The internal factor may be the kind of material, for example, the type of polymer, from which the object is manufactured; or the type of colorants or other additives, and the amount thereof, which have been included in the material. Another factor relates to the surface characteristics of the polymer 2. The present invention takes into account that the surface reflection is dependent on the observing angle ($h_1$) and the associated at least one illumination angle ($i_1$). Accordingly, an observer 10' who observes the object at the observing angle ($h_2$) under the condition of illumination under the illumination angle ($i_1$) will in general observe a different appearance than does the observer 10. According to the invention, this effect is taken into account inter alia in characterizing the appearance of an object, in predicting the appearance of an object, and in manufacturing an object with a predetermined appearance under predetermined viewing and illumination condition. The method of this invention will allow the appearance of different objects to be matched at the same or different conditions of observation such as when one of the objects is at a different angle than the other object (that is, one object is rotated in relation to the other object) or the light source at which one object may be viewed is different, for example, the wavelengths of the light hitting the object are different. More generally, it holds that the object is-manufactured such that the appearance of the object to be manufactured and that of the reference object correspond with each other at a plurality of viewing angles (h) each associated with a predetermined illumination angle (i).

It is also possible that the appearance of an object can be matched under different conditions of illumination such as different sources of light. For example, it is possible to use directional and/or a combination of directional and diffuse light or different colors of light.

In this application R(w,h,i) is the reflectance value for light with frequency (w) at the viewing angle (h) under illumination at illumination angle (i). If there are more than one illumination angles the reflectance value is also noted as R(w,h,i) as discussed for the set (h,i).

In the flow diagram of FIG. 1, which schematically depicts a preferred embodiment of this invention in which the appearance of one object (that is, the "reference object") is matched by a second object (that is, the "sample object"). In FIG. 1, block 20 designates a reference object or that object whose appearance it is desirable to match. Optionally, the reference object may not be a physical object but can be a virtual entity characterized by a desired reflectance value or range of reflectance values (or "reflectance curve") of $R_{mref}(w,h,i)$ for at least one wavelength and a pair of viewing and illumination angles.

For purposes of illustration, the reference object is also shown in FIG. 3 and designated with reference numeral 20. Using a light sensitive device 22 (FIG. 3) such as a multi-angle spectrophotometer, gonio-spectrophotometer, digital photo camera, video camera or a similar apparatus, reflectance values $R_{mref}(w,h',i')$ (or a similar quantity as produced by the various light sensitive devices) associated with a viewing angle (h') and illumination angle (i') are measured. Using the apparatus depicted in FIG. 3, $R_{mref}(w,h_2',i_2')$, $R_{mref}(Kw,h_2',i_1')$, $R_{mref}(w,h_1',i_2')$ and $R_{mref}(w,h_1',i_1')$ can be determined. Therefore, the appearance of the reference object will be determined for viewing angles (h') associated with illumination angles (i'). As depicted in FIG. 3, the viewing angle (h') is the angle enclosed between the normal 12 to a surface 4 of the object 20 and an optical axis 14 of the spectrometer.

The illuminated angle (i or i') is the angle between the optical axes 15 of the light source 6 and the normal 12. In the measuring arrangement according to FIG. 3, for determining the reflectance curve, further use is made of a light source 6 that radiates light 8. The reflectance value(s) $R_{mref}(w,h',i')$ is dependent on the viewing angle (h'), the illumination angle (i') and the frequency (w) of the light observed by the spectrometer. In this example, all measurements and calculations are carried out for one value of the frequency (w). It is however also possible to do the same measurements and the same calculations for a plurality of values of (w).

With respect to FIG. 3, the term illumination angle is to be understood as representing illumination with a certain spatial angle around the angle i, but it also includes a set up where illumination is performed by a range of well defined angles i. Also, any observing angle will typically have a certain spatial angle associated with h. As mentioned, this is noted as the set (h,i).

Returning to FIG. 1, presently in block 24 a number of reflectance values $R_{mref}(w,h',i')$ are determined for the reference object 20. With reference to the embodiment in FIG. 3, two reflectance values R(w, h', i') are determined for h'=h'$_1$, and h'=h'$_2$. The reflectance value $R_{mref}(w,h',i')$ does not need to be determined for the entire spectrum of visible light. For instance, a number of values of a frequency (w) of the reflected light from the object as received by the spectrometer may suffice. As is obvious, wavelength or angular frequency can be used in place of frequency for the purposes of this invention.

With reference to FIG. 1, the sample object 35 can be matched to a reference object in the following manner.

To that end, in block 26 of FIG. 1, a test object 26 is manufactured. Next, in block 28, the reflectance curve $R_{mtest}(w,h,i)$ of the test object is measured, associated with the viewing angle (h) under the condition of illumination at illumination angle i. The determination of the reflectance curve $R_{mtest}(w,h,i)$ can be carried out with the arrangement according to FIG. 3 or any equivalent arrangement.

As used in the embodiment depicted in FIG. 1, the material can be a polymer having certain colorants. The material is characterized by the absorption coefficient $K_{pol}(w)$ of the material and the scattering coefficient $S_{pol}(w)$. The colorants, and for the purposes of FIG. 1, it has been assumed that two colorants are employed, each are characterized by an the absorption coefficient $K_{pig1}(w)$ and $K_{pig2}(w)$ and a scattering coefficient $S_{pig1}(w)$ and $S_{pig2}(w)$. The colorants are preferably chosen such that the test object has a deep black color. In this example, the choice of the dyes is made in block 32.

The absorption coefficient $K_{tot}(w)$ colorants and the scattering coefficient $S_{tot}(w)$ of the material including the colorants is calculated in block 33 in a manner known per se, for example as follows:

$$K_{tot}(w) = C_{pig1}K_{pig1}(w) + C_{pig2}K_{pig2}(w) + C_{pol}K_{pol}(w)$$

Similarly, the total scattering coefficient of the material to which the colorants have been added can for example be calculated according to the following formula known per se:

$$S_{tot}(w) = C_{pig1}S_{pig2}(w) + C_{pig2}S_{pig2}(w) + C_{pol}S_{pol}(w)$$

In these formulae, $C_{pig1}$, $C_{pig2}$ and $C_{pol}$ represent the concentrations of the first type of dye, the second type of dye and the polymer, respectively.

Next, in block 30, on the basis of the color characterizing parameters of the selected material of the test object such as the absorption coefficient $K_{tot}(w)$ of the material of the test object and the scattering coefficient $S_{tot}(w)$ of the material of the test object, and on the basis of the reflectance value $R_{mtest}(w,h,i)$ measured in block 28, associated with the viewing angle (or angles) (h), the surface reflection $k_1(w,h,i)$ associated with the viewing angle (h) and illumination angle (i) is calculated. These calculations can be carried out using a number of different known equations which relate reflectance to the parameters $K_{tot}(w)$ and $S_{tot}(w)$, or to other color determining parameters. One method of calculation uses the Kubelka-Munk equation and Saunderson equations. For example, in block 30.1, on the basis of the known parameters $K_{tot}(w)$ and $S_{tot}(w)$ of the material of the test object, the idealized reflectance value $R_i(w)$ can be calculated on the basis of the Kubelka-Munk equation, known per se, as follows:

$$R_i(w) = 1 + \frac{K_{tot}(w)}{S_{tot}(w)} - \left(\frac{K_{tot}(w)^2}{S_{tot}(w)^2} + \frac{2K_{tot}(w)}{S_{tot}(w)}\right)^{1/2} \quad (1)$$

This equation is considered to be valid for diffuse illumination.

Next, in block 30.2, the Saunderson equation, known per se, is used. This equation is also considered to be valid for diffuse illumination. It reads:

$$R_m(w) = k_1(w) + \frac{(1 - k_1(w))(1 - k_2)R_i(w)}{1 - k_2 R_i(w)} \quad (2)$$

In this equation $R_m(w)$ is the angle independent reflectance value as it can be measured in a known manner. (Reflectance $R_m(w)$ is the measured ratio of reflected to incident light flux). Furthermore, $k_1(w)$ is the fraction of the diffuse incident light which is reflected from the front surface of the sample as known in the art (J. L. Saunderson, J. Optical soc of America, Vol 32, 12, pp. 727–736) and $k_2$ is the internal surface reflection coefficient (or the fraction of the light incident diffusely upon the surface of the samples from the inside that is reflected). The constant $k_2$ has been empirically determined many times in the past and lies in the range from 0.4–0.6 and its specific value is not critical to the application of the present invention. In general, 0.4 is typically selected for $k_2$.

Equation 2 can be rewritten where one occurrence of $k_1(w)$ (that $k_1(w)$ associated with the light reflected from the surface of the object) is replaced with $k_1(w,h,i)$, and the other occurrence $k_1(w)$ is not replaced by $k_1(w,h,i)$ and $R_m(w)$ is replaced with $R_{m_{test}}(w,h,i)$ to give formula 3:

$$R_{m_{test}}(w, h, i) = k_1(w, h, i) + \frac{(1 - k_1(w))(1 - k_2)R_i(w)}{1 - k_2 R_i(w)} \quad (3)$$

wherein $R_m(w,h,i)$ is an illumination and viewing angle dependent surface reflection. The value of $k_1(w)$ can be calculated by Fresnel's equation (see Judd, Wyszecki, Color in business, science and Industry, J. Wiley, New York, 1975, p 397–401).

Equation 3 has been written such that it has validity for directional illumination in contrast to diffuse illumination, for which equation 2 was explicitly derived, thus determining a viewing and illumination angle-dependent measured reflection coefficient $k_1(w,h,i)$ on the basis of a viewing and illumination angle-dependent reflectance value $R_m(w, h, i)$. In other words, the equation known per se, which has been assumed to be valid only for the condition of illumination by means of diffuse light, after the described modification, is also considered to be valid for specific combinations of viewing angles (h) using directional illumination. When using the Saunderson equation, in block 30.2 the following formula is then applied:

$$k_1(w, h, i) = R_{m_{test}}(w, h, i) - \frac{(1 - k_1(w))(1 - k_2)R_i(w)}{1 - k_2 R_i(w)} \quad (4)$$

Thus, the reflection coefficient $k_1(w,h,i)$ for the viewing angle h and illumination angle i, can be calculated, based on the measured $R_{m\ test}$, the $R_i$ calculated from the known formulation of the test object, and the known $k_1$ and $k_2$.

Presently, in block 34, it is predicted what will be the appearance of a sample object 35, in this case the object to be manufactured, when this object has been manufactured from the above-mentioned predetermined material with the above-mentioned predetermined surface texture and with a selection of predetermined colorants. In block 34.1, a choice is made of colorants that will be added to the material from which the object is manufactured. In the example illustrated by FIG. 1, we assume again for purposes of illustration only, that two kinds of colorants are added. The first colorant is characterized by the absorption coefficient $K_{pig1}(w)$ and the scattering coefficient $S_{pig1}(w)$. The second colorant is characterized by the absorption coefficient $K_{pig2}(w)$ and the scattering coefficient $S_{pig2}(w)$. Further, the material, known as such, from which the object is manufactured is characterized by the scattering coefficient $S_{pol}(w)$ and the absorption coefficient $K_{pol}(w)$. According to the color theory, known as such, presently the absorption coefficient of the material to which the colorants have been added can for example again be calculated as follows:

$$K_{tot}(w) = C_{pig1} K_{pig1}(w) + C_{pig2} K_{pig2}(w) + C_{pol} K_{pol}(w) \quad (5)$$

Similarly, the total scattering coefficient of the material to which the colorants have been added can for example again be calculated according to the following formula, known per se:

$$S_{tot}(w) = C_{pig1} S_{pig2}(w) + C_{pig2} S_{pig}(w) + C_{pol} S_{pol}(w) \quad (6)$$

In the formulae 5 and 6, $C_{pig1}(w)$, $C_{pig2}(w)$ and $C_{pol}(w)$ represent the concentrations of, respectively, the first colorant, the second colorant and the polymer from which the object will be manufactured. In this example, the calculation of the values of $K_{tot}$ and $S_{tot}$ is carried out in block 34.2 for at least one wavelength but preferably for a number of wavelengths. Next, on the basis of $K_{tot}$ and $S_{tot}$, in block 34.3 the idealized reflectance $R_i(w)$ of the object is calculated for at least one wavelength but preferably for a number of wavelengths. When a number or range of wavelengths is used, a reflectance curve can then be generated. The calculation is carried out on the basis of equations known per se, such as, in this example again, the Kubelka-Munk equation. Multi-flux theories and other color theories can be used as well. The idealized reflectance $R_i(w)$ can thus be calculated on the basis of formula 1.

Next, in block 34.4, on the basis of the idealized reflectance $R_i(w)$ of the object, the observed appearance viewed at the predetermined combination of viewing angle(s) (h) will be predicted by predicting what the reflectance value or curve $R_p(w, h, i)$ will be on the basis of the above-mentioned idealized reflectance $R_i(w)$ and the reflection coefficient $k_1(w, h, i)$. This calculation is again carried out with an equation known per se, this equation known per se having been assumed to be valid only for diffuse illumination and defining a relation between the idealized reflectance, an illumination-angle-independent surface reflection $k_1(w)$ and an angle-independent reflectance $R_p(w)$. By way of example, the Saunderson equation (formula 2) is used again here, with $R_p(w,h,i)$ being determined using this equation by setting $R_p(w,h,i) = R_m(w)$ and one $k_1(w)$ is replaced by the value $k_1(w,h,i)$ in this equation.

According to the invention, presently formula 2 is converted to:

$$R_p(w, h, i) = k_1(w, h, i) + \frac{(1 - k_1(w))(1 - k_2)R_i(w)}{1 - k_2 R_i(w)} \quad (7)$$

Thus it is predicted in block 34.4 what will be the reflectance value $R_p(w,h,i)$ or curve of the sample object to be manufactured.

The question is presently whether with the first choice of the colorants made, the predicted reflectance value $R_p(w,h,i)$ at the predetermined viewing angle(s) (h and illumination angle(s) (i) will correspond with the reflectance curve $R_{mref}(w,h',i')$ of the reference object and as determined in block 24. In this example the following selection is made: $R_{mref}(w,h',i') = R_{mref}(w,h,i)$. In other words, the object to be manufactured should have a reflectance value $R_{mref}(w,h,i)$ because of the predetermined demand that h=h' and i=i'. Therefore $R_{mref}(w,h,i)$ is compared with $R_p(w, h, i)$. This comparison is carried out in block 36 in a manner known per se. When the difference determined in block 36 exceeds a predetermined value, it can be fed back via a line 38 to a block 34.1 where a different choice of type or amount of colorants is made then with a view to reducing the difference referred to. On the basis of new choices, the method steps of blocks 34.1, 34.2, 34.3 and 34.4 are traversed again to obtain newly calculated reflectance value(s) or curve $R_p(w,h,i)$. Thereupon, in block 36, the difference referred to can be determined again. When the difference is still greater than the threshold value referred to, it can again be fed back via line 38 to block 34.1 where a new selection of colorants is made then. This entire process can be repeated a number of times until it appears in block 36 that the difference lies below a predetermined value. In that case, it is known in what way an object can be manufactured, since the choice of the colorants, the concentrations thereof, the choice of the polymer and the concentrations thereof, as well as the surface texture to be manufactured are known.

It holds further that the reflectance curve $R_{mref}(w,h,i)$ can for example be used for deriving, in a manner known per se, the known color defining parameters $L_{ref}$, $a_{ref}$, $b_{ref}$. For example the L, a and b values are defined by CIE (see CIE Publication NR 15.2, 1986 Vienna PO Box 169, Austria). This calculation is carried out in block 42. On the ground of $R_p(w,h, i)$ of the object to be manufactured the corresponding values $L_p$, $a_p$, $b_p$ can be determined accordingly. This calculation is carried out in block 42. On the basis of the values calculated in blocks 40 and 42, it is then possible, in block 36, to determine the parameter $\Delta E(w, h, i)$, determining said difference according to the formula:

$$\Delta E(w,h,i) = \sqrt{\Delta L^2 + \Delta a^2 + \Delta b^2} \qquad (8)$$

with $\Delta L = L_p - L_{ref}$
$\Delta a = a_p - a_{ref}$
$\Delta b = b_p - b_{ref}$ Alternatively the Delta E calculation may involve the use of the various other color difference equations known in the art.

It is noted that color matching using color prediction equations as such is known. However, this never involves predicting and matching appearance depending on the viewing and illumination angles. This means that the comparison in block 36, as well as the determination of a new choice of colorants and/or concentrations thereof can be carried out for one predetermined viewing angle (h) associated with at least one predetermined illumination angle with a color match program known per se.

Using the method of the present invention, the appearance of the reference object and that of the sample object can be matched at a number of different conditions such as a particular set of angles (h, i).

In this invention, the process is conducted using more than one set of angles (h,i). This means that in block 28 the value of $R_{mtest}(w,h,i)$ is determined for each set of the angles (h, i). This also holds for the value of $R_{mref}(w,h',i')$ in block 24. Next, on the basis of the idealized reflectance $R_i(w)$ determined in block 30.1, in block 30.2 the value of $k_1(w,h,i)$ for each of the set of angles (h, i) is determined. Than according to a first possibility a selection of colorants is made for one set of angles (h, i) as described above (blocks 34 and 36). Next, the differences $\Delta E(w, h, i)$ are determined on the bases of selected colorants for all the other sets of angles (h,i) (blocks 34 and 36 for each set of angles (h, i). Then if any of the differences $\Delta E(w,h,i)$ exceeds a certain predetermined threshold via line 38 another selection of amount and/or type of colorants can be made. Based on this new selection each of the differences $\Delta E(w,h,i)$ may be calculated to check whether they lay all below the associated predetermined thresholds (blocks 34 and 36) for each of the sets of angles (h, i). If any of the differences $\Delta E(w,h,i)$ is above its associated threshold another selection of colorants may be made to repeat the process as described above.

The above selections can be carried out both 'by hand' and with the aid of a color match program known per se. It is therefore possible that the values of $\Delta E(w,h,i)$ found in block 36 are represented on a display and that in block 34.1 an expert, on the basis of these values, makes a new selection of the colorants and/or the concentrations thereof.

According to another possibility a separate appearance match for each set (h,i) is made by selecting colorants for each set (h,i) as discussed above. On the bases of individual selections of colorants an average selection may be made which provides a match which is sufficient close for all sets (h,i).

If it appears for any of the above described methods that it is impossible to reduce the differences $\Delta E(w,h,i)$ to below the predetermined threshold value simultaneously at all angles of interest, adjustment of the surface texture of the object to be manufactured may be considered. This adjustment, at least the choice thereof, can, for instance, be carried out by a specialist. When the surface texture has thus been altered, a new test object with the altered surface texture is manufactured. The new choice of a predetermined surface texture, such as it follows from the difference $\Delta E(w,h,i)$ or, in case of several viewing angles, from the differences $\Delta E(w,h,i)$, is indicated in FIG. 1 by the line 44. Next, on the basis of the new test object, the entire process as described above is repeated. Eventually, this should lead to a result where for each desired angle, the difference $\Delta E(w,h,i)$ lies below the predetermined threshold value associated with the respective angles.

Similarly, in order to reduce the differences $\Delta E(w,h,i)$ to below the predetermined threshold value simultaneously at all angles of interest, it may also be decided to change the kind of material from which the sample is made. In the above example this will in general imply that $C_{pol}$, $S_{pol}$ and $K_{pol}$ changes. Then again a new test object is made and the entire process is traversed again. A change of polymer will in general also result in a change of surface texture. Furthermore, it is also possible to change the sample manufacturing process or process conditions. For example, if the manufacturing process is injection molding, the molding condition may be changed. In an injection molding process also the texture or roughness of the metal tool may be changed. This also affects the surface texture of the plastic sample, so that the entire process may subsequently be traversed as with a change of polymer and/or a change of the surface texture as described above.

It is possible that the values of $\Delta E(w, h, i)$ found in block 36 are represented on a display and that in block 34.1 an expert, on the basis of these values, makes a new choice of the colorants and/or the concentrations thereof, and/or surface textures and/or kind of materials.

The difference determination $\Delta E$, which is known per se but does not take the viewing and illumination angles (h,i) into account, can be further generalized, according to the invention, by determining the difference $\Delta E(h,i;h',i')$ between the appearance of the test object for the set of (h, i) and the appearance of the reference object for the set (h', i'). The following applies:

$$\Delta E(h,i;h',i') = \sqrt{\Delta L^2 + \Delta a^2 + \Delta b^2} \qquad (9)$$

with $\Delta L = L_p(h,i) - L_{ref}(h',i')$
—$a = a_p(h,i) - a_{ref}(h',i')$
$\Delta b = b_p(h,i) - b_{ref}(h',i')$ Formula 9 can then be applied in block 36 for each of the above-described methods.

On the basis of the example outlined here, it will be clear that parts of the example of FIG. 1 also comprise methods which, based on the insight of the invention, may each be of interest for independent application. Thus, the methods of block 26, 28, 30, 32, 33 are each of interest for independent application with a view to characterizing the contribution of the surface to the appearance of a particular object.

It is possible, as described above, to match the appearance of the material at a given set of viewing/observing angles with that of a reference, by adjusting colorant levels, using different colorants, or varying the type and amount of additives. However, in some cases, it is not always possible to match appearance at every desired angle(s) or other viewing conditions. In such cases, it is possible to create surfaces with various finishes. his can be done, for example, by sandblasting the metal mold used for injection-molding plastic parts, with various types of glass or sand which methods are well know in the art. These various surfaces can now be characterized by their $k_1(w,h,i)$ curves. This allows a check as to which curve best fits that of the $R_{mref}(w,h,i)$ to be matched. The surface most closely corresponding to this curve can then be selected. Another approach is to study different polymeric materials. For example, ABS materials with different rubber morphology can be selected. These materials will have a different dependence of reflectance $R_p(w,h,i)$ on viewing/observing angle (h). In other words, different polymers will also produce differently shaped $k_1(w,h,i)$ curves as a function of the viewing angles, for a fixed mold surface (for example fixed sand type). Again, the polymer can be selected that will allow creating a match with the reference.

For example, this is possible by first making a match with a reference object (with all surfaces and at one set of viewing and illumination angles $h_1$ and $i_1$). For each surface a slightly different colorant composition may be required. Subsequently, $R_p(w,h,i)$ is calculated at a second set of viewing and illumination angles (preferably with at least one of the angles rather different from the angle used before $h_2$ and $i_2$). Then, using the same colorant composition found in the first match, one only replaces the $k_1(w,h,i)$ value corresponding to the new set of angles. Subsequently, select that surface that gives the closest match ($R_p$ close or equal to $R_{ref}$) at this second set of angles. When a good match is reached for a second set of angles, then in many cases matches will be reasonable for all sets of angles. It is also possible to combine surface variation with material variation. A full appearance match over a range of angles then consists in selecting the right polymer, recommending the right surface treatment of the metal mold and calculating the right colorant formulation.

In the manner outlined hereinbefore, a material (the choice of the polymer) and/or surface texture can be selected to form a good match with the reflectance curve $R_{mref}(w,h,i)$. After the material and/or the surface texture have been selected, the type and amount of colorants can be calculated using techniques described hereinbefore. This will assist in determining in what way the object is to be manufactured in order that the appearance of the object agrees within the predetermined limits with the appearance of the reference object and/or the reference reflectance curves.

As indicated, the test object is manufactured from a selected material and surface texture corresponding with that of the sample to be manufactured. It is however also possible that the surface contribution to appearance or the at least one surface reflection $k_1(w,h,i)$ for the object is set without the intermediate use of the test object. Hence, in that case, with reference to FIG. 1, block 30.2 instead of block 26 would represent the starting point. Subsequently, the method is continued as discussed hereinbefore. Again, this first choice for the surface contribution to appearance or the surface reflection $k_1(w,h,i)$ may be fixed. However the choice of the surface contribution to appearance or the surface reflection $k_1(w,h,i)$ for the object may also be adjusted in view of the difference information, whereafter the colour matching steps as discussed before are repeated. This process of adjustment may also be repeated until the difference information lies below a predetermined value. Finally, in block E the sample is actually made in the laboratory with the composition determined by above described iteration in 34.1 and the finally selected material and surface texture of the final test object. Then, in 39 the reflectance values of the sample, $R_{sample}(w,h,i)$ are measured, and used to calculate Lab values in 42, which are compared with the Lab values of the reference object in block 36. If the Delta E values in 36 are within acceptable limits, the process of appearance matching can be considered to be completed successfully. However, due to experimental error in all K, S and other data, and other factors, it may be that there is a need to further refine the match. In this case all options described above (change in material, colorants, textures etc.) can be used to get an even closer appearance match and steps 35 and 39 are repeated until the match is acceptable.

Furthermore, the invention applies generally to color theories other than those discussed above. Thus, instead of the Saunderson equations and the Kubelka-Munk equation, other equations known per se can be used or can be used after slight modification. Also, instead of the scattering $S_{tot}$ and the absorption $K_{tot}$, other parameters known per se which characterize the color of the object can be used. What remains, however, is that the prediction of what the color of an object will be, the matching of the appearance of an object with another object, etc., is carried out in each case depending on the sets of angles (h,i) and that surface contribution is separated from internal color.

The surface contributions to appearance, or the surface reflections $k_1(w,h,i)$, may also be calculated from a plurality of reflectance values $R_m(w,h,i)$ which are measured for at least one light frequency w and at least two predetermined viewing angle (h) under the condition of illumination with diffuse light.

It is also possible to predict the appearance of transparent of translucent objects in reflectance or in transmittance in a manner as discussed above. Furthermore the surface reflection value(s) $k_1(w,h,i)$ may be calculated from a knowledge of the surface topology of the given texture of the object.

Such variants are all understood to fall within the scope of the invention.

The following example is presented to illustrate the present invention and is not intended to limit its scope and should not be so interpreted. Amounts are in weight percentages unless otherwise indicated.

EXAMPLE

It was desired to match the appearance of a reference object that was an acrylonitrile, butadiene, styrene (ABS) copolymer having a blue grey (color nr 41936) grained (type 0000.33) plastic surface. The reflectance values of the material were measured on a multi-angle spectrophotometer of GretagMacbeth type ER50, under three aspecular angles of 20, 45 and 75 degrees.

A mixture was compounded containing the same ABS copolymer and the following colorants identified by their Colour Index numbers: C.I.61710 at 0.1 percent, C.I.Solvent Red 135 at 0.2 percent, C.I.47020 at 0.1 percent, and C.I.Solvent Green 28 at 0.2 percent, the percentages based on the weight of the ABS copolymer to prepare a black material. (Colour Index numbers are published by the Society of Dyers and Colourists, Bradford, England with the American Association of Textile Chemists and Colorists, North Carolina 27709 USA). A molding was made from this material on the same mold with grain 0000.33. The reflectance values were measured using a multi-angle spectrophotometer of GretagMacbeth type ER50, under three aspecular angles of 20, 45 and 75 degrees. These reflectance curves were used to calculate the $k_1$ value in the Sanderson equation as described previously. The absorption coefficient K and scattering coefficient S, are known for each of the dyes when used in this ABS copolymer. The Kubelka-Munk equation was used to combine calcuated $k_1$ values with these K and S coefficients, and to calculate the pigment formulation that would produce the right appearance.

An ABS formulation having C.I.77891 at 0.176 percent, C.I.77310 at 0.016 percent; C.I.77491 at 0.042 percent; C.I.77007 at 0.335 percent and C.I.77266 at 0.0085 percent was determined to have the same reflectance value with the $k_1$ value that had been calculated.

This formulation was prepared and compounded on a twin screw extruder. The material was then injection molded in grain 0000.33 and measured on the multi-angle spectrophotometer. The following CieLab Delta E color differences were obtained (illuminant D65 and 10 degrees observer; Delta E) at the following angles:
20 degrees: 2.41
45 degrees: 1.05
75 degrees: 0.34
These Delta E values are normal for color matching. As such, the formulation was shown to have the selected appearance under those 3 angles and, in normal practice, it would be possible to create a even closer match by adjusting the colorant formulation.

What is claimed is:

1. A method for characterizing a surface contribution to an object's appearance; the method comprising determining from the object surface reflection values $k_1(w,h,i)$, from a plurality of reflectance values $R_m(w,h,i)$ which are established for at least one light frequency (w) and a plurality of combinations of viewing (h) and illumination (i) angles.

2. The method according to claim 1 wherein the surface reflection values $k_1(w,h,i)$, are calculated from at least two different reflectance values $R_m(w,h,i)$ established for a predetermined combination of viewing and illumination angles using directional light.

3. The method of claim 1 wherein $k_1(w,h,i)$ values are calculated from idealized reflectance value(s) $R_i(w)$ for light frequency or frequencies (w), and the measured reflectance values $R_m(w,h,i)$ using a color theory equation.

4. The method of claim 3 wherein the color theory equation has been assumed to be independent of the viewing and illumination angles and defines a relation between the idealized reflectance value(s) $R_i(w)$, a viewing and illumination angle-independent surface reflection value(s) $k_1(w)$, and reflectance value(s) $R_m(w)$ which are measurable independently of the viewing and illumination angles, with $k_1(w,h,i)$ being calculated by substituting one occurrence of $k_1(w)$ with $k_1(w,h,i)$ and replacing $R_m(w)$ with $R_m(w,h,i)$ in this equation, and subsequently calculating $k_1(w,h,i)$ from this equation.

5. The method of claim 4 characterized in that each surface reflection value $k_1(w,h,i)$ is calculated by solving $k_1(w,h,i)$ from said equation for each value of $R_m(w,h,i)$ and the value(s) of $R_i(w)$.

6. The method of claim 4 wherein the object has a black color.

7. A method for predicting an appearance of an object wherein the method comprises predicting the appearance of the object at predetermined viewing (h) and illumination (i) angles and at least one light frequency (w) based on color determining parameters of the material from which the object is manufactured and a plurality of surface reflection values $k_1(w,h,i)$ that represent a surface contribution to the appearance for a predetermined plurality of combinations of viewing and illumination angles and at least one light frequency (w).

8. The method according to claim 7 wherein, an idealized reflectance value $R_i(w)$ of the object is calculated based on the color determining parameters of the material from which the object is manufactured and subsequently a prediction of observed appearances for the object as viewed at a plurality of combinations of viewing and illumination angle(s) by calculating a plurality of reflectance values $R_p(w,h,i)$ using the viewing and illumination angle(s), the reflectance value $R_p(w,h,i)$ being calculated using an equation from a color theory, the equation being assumed to be independent of the viewing and illumination angles and defining a relation between the idealized reflectance value $R_i(w)$, an angle-independent surface reflection $k_1(w)$ and an angle-independent reflectance value $R_p(w)$, with $R_p(w,h,i)$ being calculated at a combination of viewing and illumination angles and by setting $R_p(w,h,i)$ equal to $R_p(w)$ and replacing one $k_1(w)$ with $k_1(w,h,i)$ in this equation and by subsequently solving $R_p(w,h,i)$ from this equation using the idealized reflectance $R_i(w)$ and the surface reflection $k_1(w,h,i)$.

9. The method according to claim 8 wherein the values of $k_1(w,h,i)$ are determined from a test object manufactured from a material and with a surface texture corresponding to the kind of material and predetermined surface texture of a sample object to be made in a later stage.

10. The method according claim 9 wherein an appearance of the sample object is predicted at a plurality of combinations of predetermined viewing and illumination angles based on the color determining parameters of the material from which the sample object is manufactured and the plurality of reflection values $k_1(w,h,i)$ obtained from the test object for a plurality of combinations of viewing and illumination angles.

11. The method according to claim 10 wherein the plurality of surface reflection values $k_1(w,h,i)$ obtained from the test object are respectively determined from a plurality of corresponding reflectance values $R_1(w,h,i)$ of the test object.

12. The method of claim 11 wherein the test object has a black color.

13. A method for matching an appearance of an object with a reference object; the method comprising the steps of:
   (a) measuring or otherwise selecting reflectance values $Rm_{ref}(w,h,i)$ of the reference object using at least one light of frequency (w) and a plurality of predetermined viewing angles (h) and illumination angles (i);
   (b) measuring reflectance values $R_{mtest}(w,h,i)$ of a test object manufactured by a pre-selected method from a pre-selected material having a pre-selected amount and type of colorant(s) and/or other additive(s);
   (c) calculating values for a surface contribution to appearance $k_1(w,h,i)$ of the test object from reflectance values $Rm_{test}(w,h,i)$;
   (d) making a sample object with predicted reflectance values $R_p(w,h,i)$ by selecting a surface texture similar to that of the test object and characterized by $k_1(w,h,i)$ values and a composition such that $R_p(w,h,i)$ values that are predicted to be similar to $R_{ref}(w,h,i)$ values;
   (e) comparing the reflectance values measured on the sample object from step (d) with those the reference object; and
   (f) repeating, as desired, steps (b), (c), (d), and (e) changing the surface texture the amount or type of colorants, other additives or manufacturing process until the appearance match between the first and second object is acceptable.

14. The method according to claim 13 wherein the test object in step (b) has a black color.

15. The method of claim 13 wherein the surface reflection values $k_1(w,h,i)$ of the test object are determined based on a preselected material and surface texture.

16. The method according to claim 13 wherein a test object is manufactured from a preselected material and surface texture and the value(s) $k_1(w,h,i)$ for the viewing and illumination angle(s) is calculated by solving $k_1(w,h,i)$ for each value of $R_m(w,h,i)$ and an idealized reflectance value $R_t(w)$ from a color theory equation that has been assumed to be independent of viewing and illumination angles and that defines a relation between $R_t(w)$, a viewing and illumination angle-independent surface reflection $k_1(w)$, and a reflectance value $R_m(w)$ which is measurable independently of the viewing and illumination angles, where $k_1(w,h,i)$ substitute for $k_1(w)$ in one occurrence and $R_m(w)$ is replaced by $R_m(w,h,i)$ in the equation.

17. The method according to claim 13 wherein the surface reflection values $k_1(w,h,i)$ do not change in step (f).

18. The method according to claim 13 wherein the material does not change in step (f).

19. The method of claim 13 wherein:

step (c) comprises the steps of calculating an idealized reflectance value $R_t(w)$ of the test object using an equation from a color theory, independent of the viewing and illumination angles h,i, using color determining parameters of the material from which the test object is manufactured that are dictated by what material and added colorants and/or other additives comprise the test object, and step (d) comprises calculating $R_p(w,h,i,)$ using an equation from a color theory, which equation has been assumed to be independent of the viewing and illumination angles and that defines a relation between the idealized reflectance value(s) $R_t(w)$, angle-independent surface reflection value(s) $k_1(w)$ and angle-independent reflectance value(s) $R_p(w)$ such as it would be measured, with $R_p(w,h,i)$ being determined using this equation by setting $R_p(w,h,i)$ equal to $R_p(w)$ and one $k_1(w)$ is changed to $k_1(w,h,i)$ in this equation and by subsequently solving $R_p(w,h,i)$ from this equation on the basis of the idealized reflectance value(s) $R_t(w)$ and the surface reflection $k_1(w,h,i)$.

20. The method of claim 19 wherein the color determining parameters are calculated from absorption coefficient $K_{pol}$ and scattering coefficient $S_{pol}$ of a polymer comprising an object and absorption coefficient $K_{pig}$ and scattering coefficient $S_{pig}$ colorants and/or other additives comprising an object, wherein the object is the test object for step (c) and the sample object for step (d).

21. The method of claim 19 wherein the $R_{mref}(w,h,i)$ values are determined from a reference object.

22. The method of claim 19 wherein the method is carried out for a plurality or a range of values for the frequency (w).

23. The method of claim 13 wherein the sample object is transparent or translucent.

* * * * *